United States Patent [19]

Brown

[11] Patent Number: 5,695,492
[45] Date of Patent: *Dec. 9, 1997

[54] LAMELLAR ILLUMINATION APPARATUS FOR EYE SURGERY

[76] Inventor: Alan W. Brown, 4220 Forwalt Pl., Wilmington, N.C. 28409

[*] Notice: The term of this patent shall not extend beyond the expiration date of Pat. No. 5,582,608.

[21] Appl. No.: 748,056

[22] Filed: Nov. 13, 1996

Related U.S. Application Data

[63] Continuation-in-part of Ser. No. 420,129, Apr. 11, 1995, Pat. No. 5,582,608.

[51] Int. Cl.⁶ .................................................. A61N 5/06
[52] U.S. Cl. ............................................................ 606/4
[58] Field of Search ......................... 606/2, 4, 5, 6, 606/11, 15, 16, 17, 10, 12

[56] References Cited

U.S. PATENT DOCUMENTS

| | | |
|---|---|---|
| 4,905,711 | 3/1990 | Bennett et al. ............ 606/4 |
| 5,092,863 | 3/1992 | Schanzlin .................. 606/5 |
| 5,102,409 | 4/1992 | Balgorod ................... 606/5 |
| 5,108,412 | 4/1992 | Krumeich et al. ......... 606/4 |
| 5,133,708 | 7/1992 | Smith ........................ 606/5 |
| 5,141,506 | 8/1992 | York ......................... 606/5 |
| 5,425,727 | 6/1995 | Koziol ...................... 606/5 |
| 5,437,658 | 8/1995 | Muller et al. ............. 606/5 |
| 5,490,849 | 2/1996 | Smith ........................ 606/5 |
| 5,582,608 | 12/1996 | Brown ...................... 606/4 |

*Primary Examiner*—Jennifer Bahr
*Assistant Examiner*—Sonya Hans-Ogugua
*Attorney, Agent, or Firm*—John R. Duncan; Front D. Gilliam

[57] ABSTRACT

Apparatus for illuminating a central area of an eye by generally lamellar lighting during eye surgery. Basically, a support fixture carrying a light emitter is adapted to be placed adjacent to the surgical field. The support fixture, when in place on an eye, directs light from the light emitter toward the surgical field tangentially to the cornea, at an angle of from about 0° to 90° to the plane of the eye iris. The light entering the eye travels along the lamellae of the cornea in the manner of a light pipe. Very little, if any light reaches the back of the eye, avoiding patient discomfort, or is directed toward the surgical microscope as glare. This generally lamellar lighting combines scleral scatter and retro illumination. In preferred embodiments, the light emitter may be mounted on, or incorporated in, a conventional eyelid speculum or a fixation ring.

25 Claims, 5 Drawing Sheets

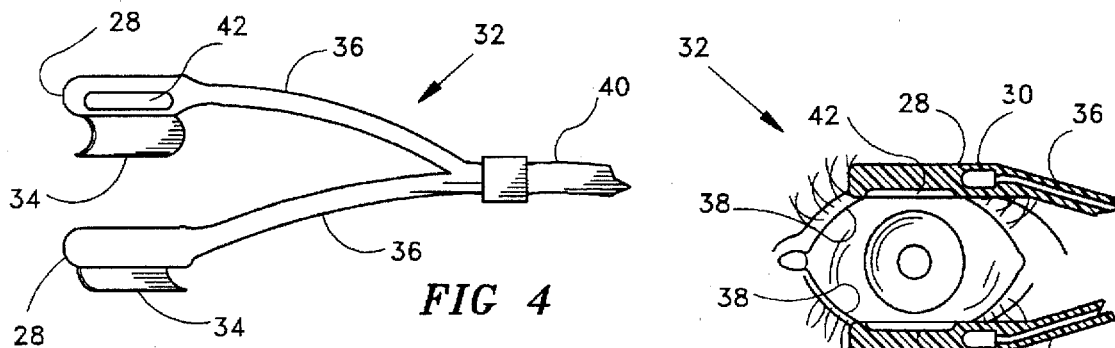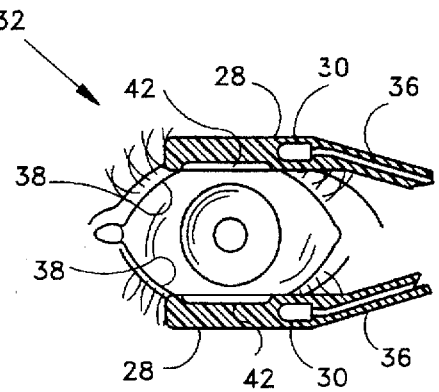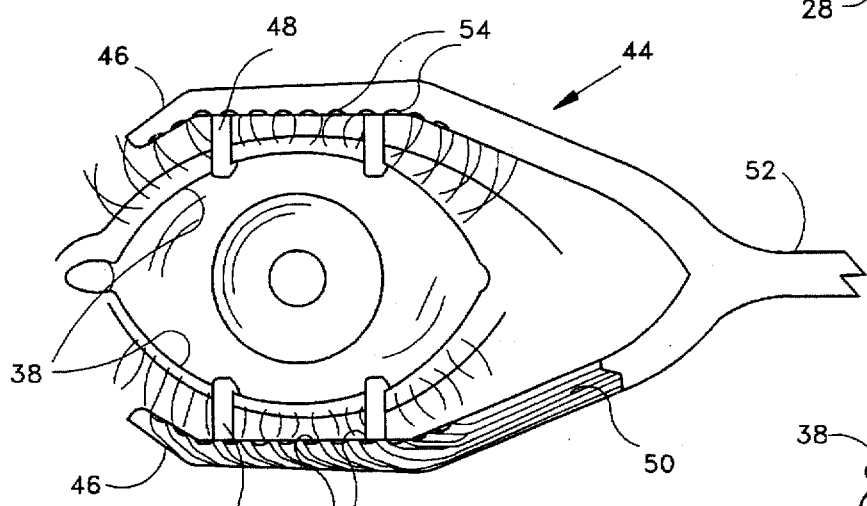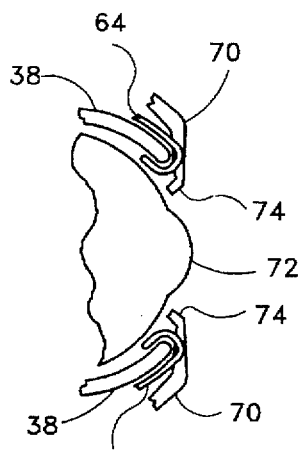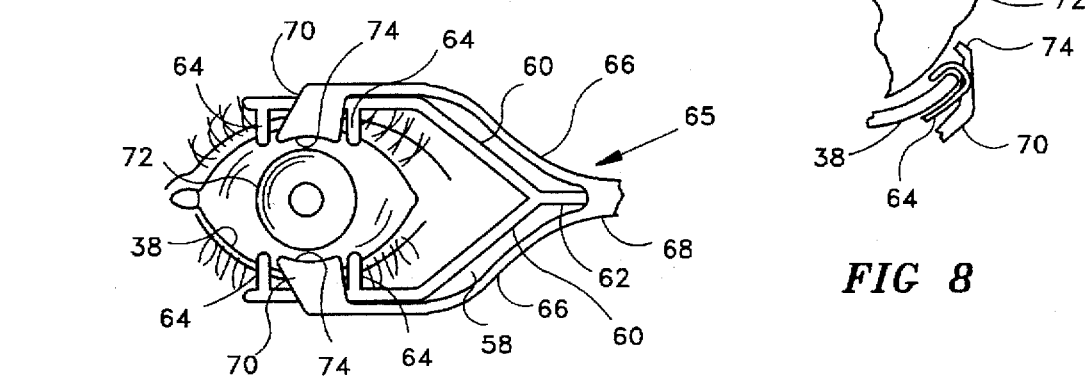

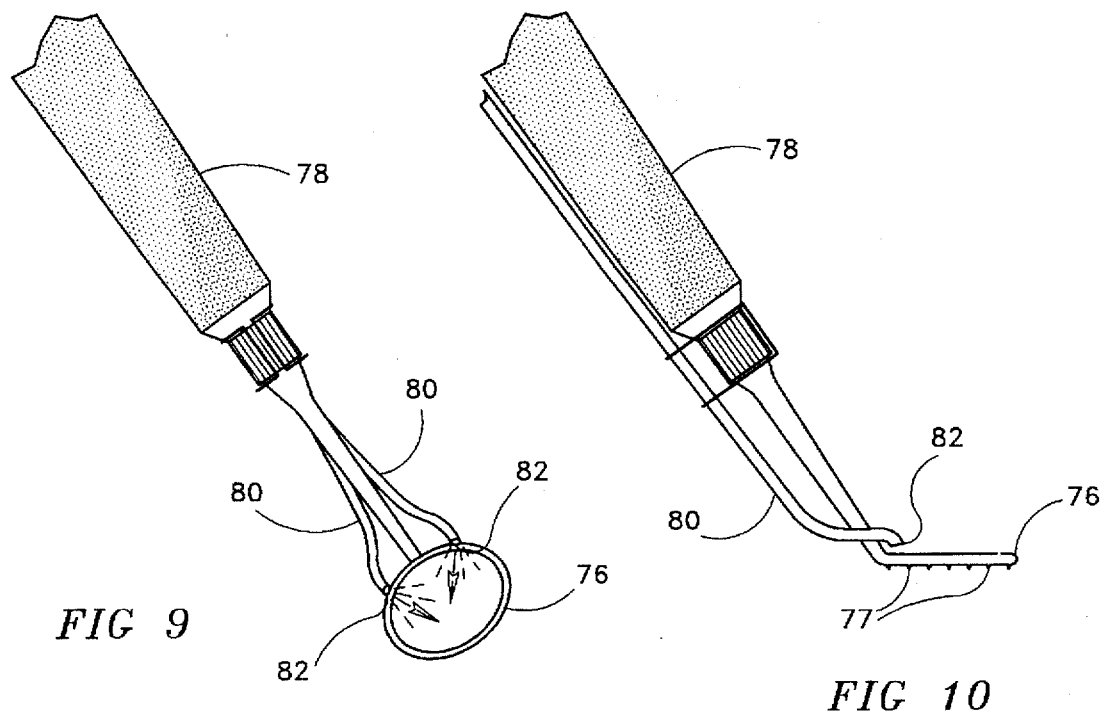
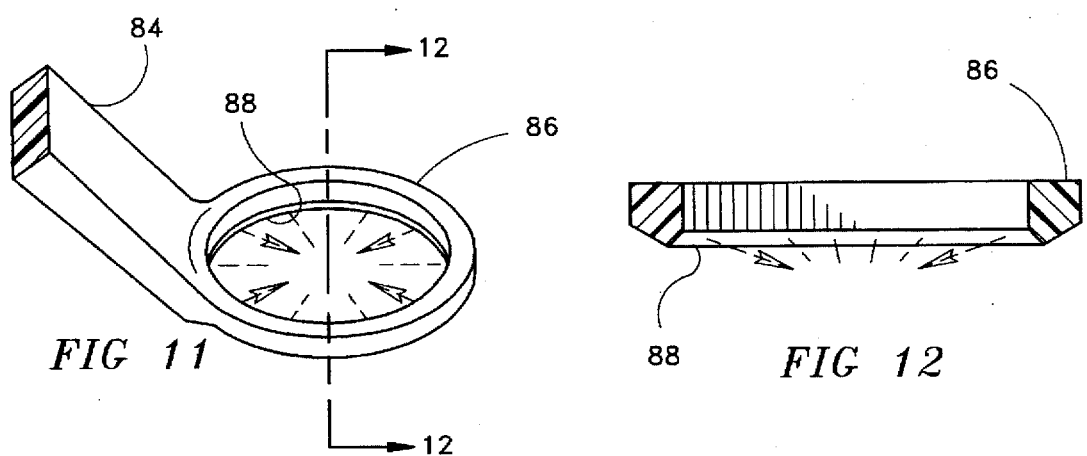

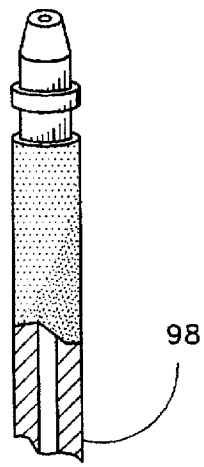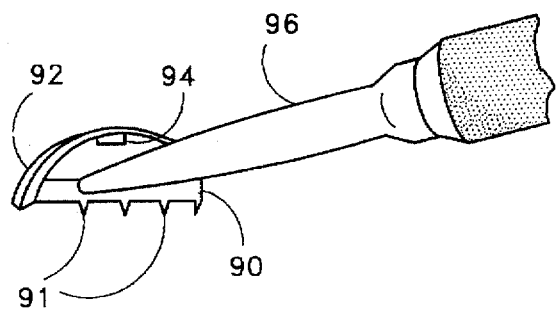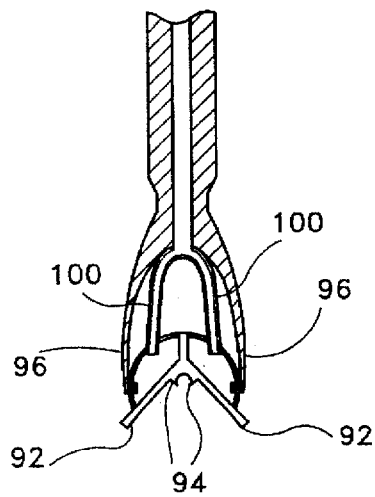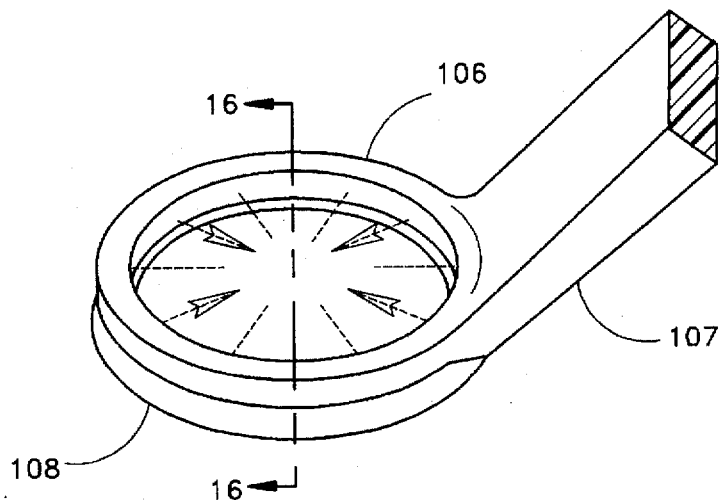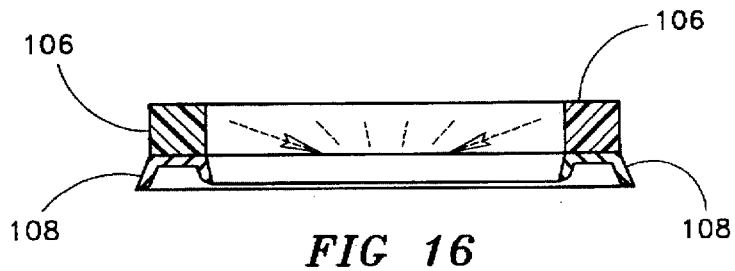
FIG 13
FIG 14
FIG 15
FIG 16

LAMELLAR ILLUMINATION APPARATUS FOR EYE SURGERY

This application is a continuation-in-part of application application Ser. No. 08/420,129 now U.S. Pat. No. 5,582,608 filed on Apr. 11, 1995.

BACKGROUND OF THE INVENTION

This invention relates in general to apparatus for illuminating an eye undergoing eye surgery and, more specifically, to an apparatus for illuminating an eye by generally lamellar illumination, combining scleral scatter and retroillumination, during surgery such as radial keratotomy, astigmatic keratotomy, cataract removal and the like.

Conventionally, coaxially operating room microscope illumination is used to view the surgical field during eye surgery. Because of observed phototoxic effects of coaxial illumination, various filters or light-dimming techniques have been developed to reduce those effects. Still, the operating room microscope places significant light coaxial into the patient's visual axis, which can result in retinal phototoxicity, patient discomfort and corneal drying.

Illumination approaching perpendicular directly over the pupil enters the eye directly through the pupil and stimulates the most sensitive back surface of the eye. This results in a patient sensation of extreme brightness, associated discomfort and tearing.

Axial lighting requires high levels of illumination and the reflected light image must compete with the glare from the projected light. The surgeon can experience difficulties during a procedure with glare that emanates from the axial light source reflecting from the anterior surface of the eye or associated structures and instrumentation.

The high intensity of axial light is often associated with a drying effect on the anterior structures of the eye secondary to a drying effect on the tear film. This drying can alter the thickness of the cornea and health of the surface tissue of the cornea (corneal epithelium), which in the setting of refractive surgery can result in serious surgical errors and complications. Further, phototoxicity of the posterior structures of the eye (retina) can occur with the use of strong axial microscope lighting and can cause permanent vision loss.

Thus, there is a continuing need for improved eye illumination apparatus which reduces light intensity, reduces drying effects to the eye decreases the light reaching the back of the eye to reduce patient discomfort and essentially eliminate phototoxicity, reduces glare and light reflected back into the microscope ocular, and provides improved visualization of the surgical field and instrument position.

SUMMARY OF THE INVENTION

The above-noted problems, and others, are overcome in accordance with this invention by an apparatus for illuminating the eye that includes a support means in contact with the eye surface adjacent to, or surrounding, the surgical field and light emitting means on the support for directing light toward the surgical field at an angle of from about 0° to 90° to the plane of the eye iris and in which light is directed against only portions of the cornea where light will not be reflected from the cornea surface back along the eye axis and will not directly pass to the back of the eye. Light rays will be directed at the eye along paths in a ring-like or generally tubular volume, varying from a conical ring when the angle to the iris plane approaches 0° to a cylindrical ring as the angle approaches 90° to the iris plane. The internal diameter of this ring, within which light is not directed against the eye will vary at the eye surface from just greater than the diameter of the pupil within the eye as the light angle approaches 90° to a greater diameter as the light direction approaches 0° to the iris plane.

When light is presented to the anterior surface of the eye (cornea) or at a very acute angle the cornea acts in the manner of a "light pipe", so that light entering at one edge of the cornea is bent within the cornea, passing parallel to the cornea surface to exit 180° away. Some light may be diffused through the lamellae of the cornea for a distance from the light entrance. Light that projects onto the corneal scleral junction at an acute angel will thus be directed within the corneal lamellae which act as the light diffuser or light pipe.

When light is presented to the anterior surface of the eye (cornea or sclera) in less acute angles or perpendicular to the iris plane, the light entering the eye is reflected off the iris or other eye structures and so retro illuminates the cornea and internal structures. Retro illumination provides a quality of light that enhances visibility of certain fine details and thus facilitates surgery.

Light directed perpendicular to the plane of the iris is by definition parallel to the pupillary/visual axis. However, light so directed will not enter the pupillary axis if the parallel illumination is offset from the pupillary axis. The offset allows for the advantage of retro illumination of the cornea without the disadvantages of focussed light coaxial to the pupillary axis. The offset is sufficient to prevent refraction of the offset light by the cornea into the pupillary axis.

Since the light is not directed perpendicularly through the central area of the pupil, very little light actually enters the eye to cause patient discomfort. Almost no light can enter the eye in a focused manner to reach the central posterior structure and cause photo toxicity to central vision. Similarly, there will be very little reflected light entering the microscope ocular. Instead, light refracted from the cornea projects to the microscope. Consequently, there is less glare in the visualized structures and those visualized can be seen more clearly at lower light levels. This is particularly true when the surgery involves the cornea and involves altering the shape of the cornea through optical (laser) means or when corneal lamellar structures are incised in a procedure such as radial or astigmatic keratotomy or lamellar corneal surgery. In addition, since lower light levels can be used and light enters outside the visual axis or towards the edges of the cornea the drying effect on the anterior surface of the eye is reduced.

Any of several different embodiments of apparatus for introducing light in this manner at selected eye surface locations may be used, depending on the particular circumstances.

In one preferred embodiment, light emitting means may be secured to one or both arms of a conventional eyelid speculum assembly. For the purposes of this application, an eyelid speculum assembly includes both a integral two-arm speculum or two cooperating single arm speculums. The light emitters are oriented to direct the light into the eye at the 0° to 90° angle to the iris plane in a manner preventing light from directly passing to the back of the eye or from being directly reflected back along the eye axis. The light emitting means may include fiber optics or light pipes which conduct light from a remote source to emitting ends at the speculum arms. The fiber optics or other optical system may be supported in any desired manner, such as by running through an opening in a handle or along the exterior of a handle. Incandescent bulbs, light emitting diodes, light reflected from a microscope lamp, etc. may be used to direct light into fiber optics or light pipes. If desired, bulbs or LED's and may be included in housings attached to speculum arms to more directly provide the required light. The housings may also contain batteries to power the light emitter. In general, for optimum results the light should be directed along a narrow beam or through a narrow linear slit. Focussing optics at the light emitting member can provide the desired beam profile.

In another embodiment, the light emitting means may be a part of, or attached to, a conventional fixation ring. Fiber optics or light pipes are preferred for conveying light from a source to a ring (or partial ring) shaped support which is placed against the eye surface surrounding the surgical field. Alternatively, one or more spaced emitters, such as the ends of fiber optic bundles, may be positioned at selected locations near or along a fixation ring to direct light at the specified angle toward the surgical field.

Fixation rings often have small pointed projections along the side engaging the eye to maintain the ring in place. In a preferred embodiment, a ring carrying the light emitter, typically a ring of fiber optic light exit ends or a continuous light pipe type emitter may be secured to a ring of soft rubbery material having a channel shaped cross section. The open channel is pressed against the eye and is held in place by the resulting slight vacuum, in the manner of a suction cup.

In a particularly preferred embodiment, the light emitting means may be placed on a support comprising a partial circle fixation member pivotally mounted on a handle. The fixation member includes radial guides for guiding a knife along a selected line for radial keratotomy and a stop for preventing cutting beyond a selected point when cutting toward the center of the eye, using the so-called "Russian" method. The light emitting means preferably constitutes ends of fiber optic bundles, or light focused from a high intensity source, positioned to provide light at the desired acute angle.

Another embodiment has a narrowly focussed light source support independent of a lid speculum or fixation ring, typically a simple handle with optics for focussing the light into a defined beam. The handle may be hand-held or may engage the nasal bridge or descend from a microscope.

BRIEF DESCRIPTION OF THE DRAWING

Details of the invention, and of preferred embodiments thereof, will be further understood upon reference to the drawing, wherein:

FIG. 4 is a perspective view of a laminar light emitting means mounted on an eyelid speculum;

FIG. 5 is a plan view, partially cut away, of the apparatus of FIG. 4;

FIG. 6 is a plan view, partially cut away, of a second embodiment of a laminar light emitting means mounted on an eyelid speculum;

FIG. 7 is a plan view, partially cut away, of a third embodiment of a laminar light emitting means mounted on an eyelid speculum;

FIG. 7b is a section view taken on line 7b—7b in FIG. 7a.

FIG. 8 is a left elevation view of the embodiment shown in FIG. 8;

FIG. 9 is a front elevation view of a fixation ring assembly having a laminar light emitting means;

FIG. 10 is a side elevation view of the fixation ring assembly of FIG. 9;

FIG. 11 is a perspective view of a second embodiment of a fixation ring assembly having a laminar light emitting means;

FIG. 12 is a section view taken on line 12—12 in FIG. 11;

FIG. 13 is a front elevation view of a third embodiment of a fixation ring assembly having a laminar light emitting means;

FIG. 14 is a detail side elevation view of the ring portion of the assembly of FIG. 13;

FIG. 15 is a perspective view of a fourth embodiment of a ring assembly using a light pipe light emitter and a suction mounting ring;

FIG. 16 is a section view taken on line 16—16 in FIG. 15.

DETAILED DESCRIPTION OF PREFERRED EMBODIMENTS

Figure 1:
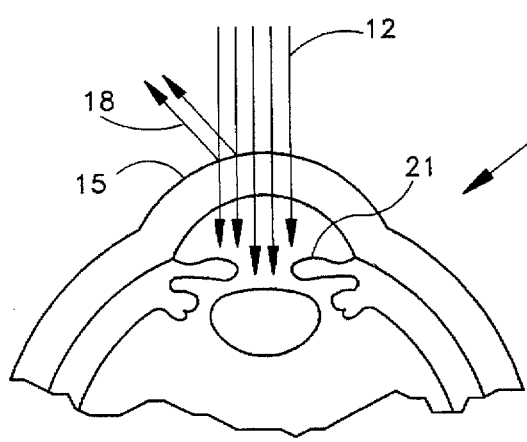
FIG. 1 is a schematic axial section view though an eye illuminated in accordance with the prior art.

FIG. 1 is an axial section through an eye 10, schematically illustrating the light path of axial lighting 12 from a conventional microscope lighting system (not shown). As shown, a portion 14 of the light passes directly through cornea 15 to the back of the eye, causing discomfort to the patient. Another portion 16 of the incident light reflects from the front surface of the eye, causing glare. Only a small part 18 of the light is reflected from incisions and the like within the iris. Thus, a surgeon must use rather intense light to receive sufficient feedback light from the areas of surgical interest.

Figure 2:
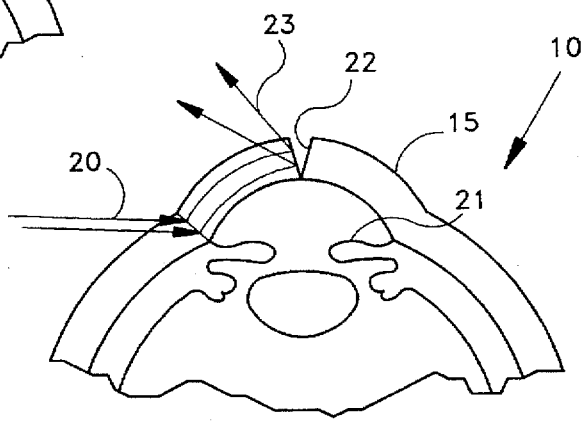
FIG. 2 is a schematic axial section view though an eye illuminated by generally lamellar lighting resulting in scleral scatter.

FIG. 2 shows the path of light 20 which enters eye 10 at an low angler nearly parallel with the plane of the iris and cornea 15. This lighting, termed "generally lamellar lighting", which is primarily scleral scatter, directs the light into the lamellae of cornea 15 where it follows the path shown until a disruption such as incision 22 is encountered to scatter light 23, making the incision particularly visible to the surgeon viewing the incision through a surgical microscope. A bright dot generally appears at the knife tip, making the precise location of the knife readily apparent.

Figure 3:
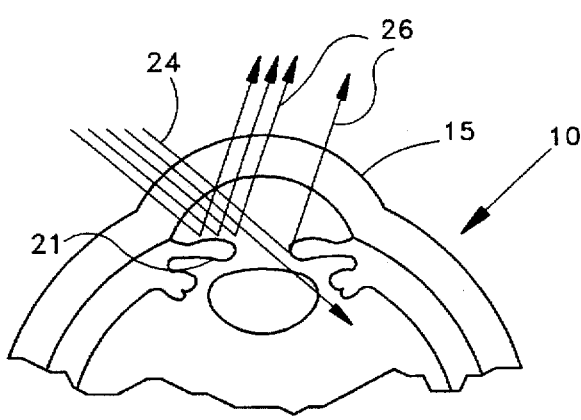
FIG. 3 is a schematic axial section view though an eye illuminated by low angle generally lamellar lighting resulting in retro illumination.

As seen in FIG. 3, some light 24 entering as retro illumination at a higher angle may pass through the cornea and be reflected at the eye interior. Light reflects off the surface of the eye at an angle that prevents direct entrance into the axis of the operating microscope and thus prevents glare. Light 26 reflected from internal structures such as iris 21 is attenuated and provides a back lit (retro illumination) of the cornea. Such illumination significantly enhances visualization of fine corneal detail. Light scattered by any object, such as an embedded foreign body, or incision in the eye or any corneal discontinuities (not shown) will scatter light in the manner shown in FIG. 2 and become visible through the microscope. Because of the acute entrance angle, only a very small portion of the entering light will reach the back of the eye, avoiding patient discomfort.

Figure 3A:
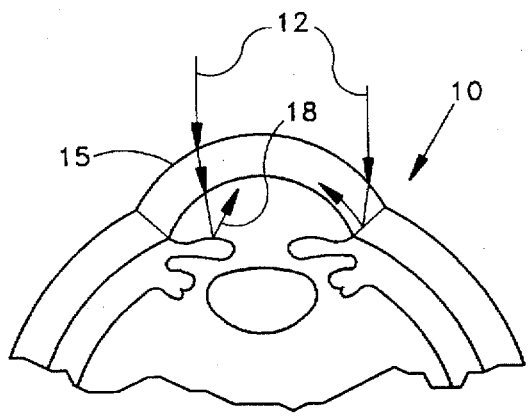
FIG. 3a is a schematic axial section view though an eye illuminated by light entering at approximately 90° to the eye plane along a ring-like path having a diameter such that light does not pas to the back of the eye.

Offset lamellar lighting is illustrated in FIG. 3a, with the lighted directed parallel to the eye axis (90° to the eye plane). This provides both retro illumination and sclerotic scatter with the benefits described above. The offset nature of the narrowly focussed beam prevents direct or refracted light from entering the pupillary axis.

Because generally lamellar lighting causes any corneal discontinuity to scatter light in the absence of associated glare, and with a relatively dark background, these discontinuities glow brightly allowing excellent visualization. For example, in incisional refractive surgery, the incisions glow and the diamond knife intercepts the light and pipes it toward the diamond tip, making the exact location of the diamond tip easily visualized. These advantages are not possible with conventional microscope lighting.

Thus generally lamellar lighting, which is a combination of scleral scatter and retro illumination, avoids significant light impact on the back of the eye and associated patient discomfort and phototoxicity. Generally lamellar lighting also avoids glare which makes viewing a surgical field through a microscope difficult. Light should enter the eye at an angle of from about 0° to 90° to the plane of the iris 21, as done by the apparatus hereinafter described. In particular circumstances, a particular angle within that range may be preferred. The iris is the contractile circular diaphragm forming the colored portion of the eye. The plane of eye iris 21 for the purposes of this application is considered to be the plane in which the outer edge of the iris substantially lies.

In a first embodiment of the apparatus of this invention, as seen in FIGS. 4 and 5, a housing 28 containing a light source 30 is mounted on, or formed as part of, a conventional eyelid speculum 32. Speculum 32 includes two arcuate members 34 mounted on arms 36 and shaped to engage and spread apart a patient's eyelids 34 to keep a central surgical field clear. Arms 36 are mounted on a handle 40.

Each housing 28 includes an elongated opening 42 oriented to direct light into the eye as shown in FIG. 2. Opening 42 may have any suitable dimensions. In general, a relatively thin slit is preferred, oriented at a predetermined angle to the eye plane within a range of from about 0° to 90°. The interior of housing 28 is preferably highly reflective. Any suitable light source 30 may be used. While a light emitting diode as shown is preferred in this embodiment, any other light source, such as incandescent bulbs, fiber optics, lasers, light pipes, electroluminescent means etc. may be used if desired.

FIG. 6 shows an alternate arrangement in which an eyelid speculum 44 includes two hollow arms 46, each of which has a pair of "U" or "J" shaped hooks 48 sized to retract eyelids from the surgical field. Fiber optic bundles 50 extend down handle 52 and along each arm 46, terminating in emitting ends 54 spaced along arms 46. The fiber optic bundles may extend within handle 52 as shown or may be supported along the handle exterior. Ends 54 are preferably in a plane radially oriented toward the center of the pupil, parallel to the iris plane when the speculum is in place. As before, the light from light emitting ends 54 enters the eye at a predetermined angle or range of angles to the plane of the iris of from about 0° to 90°. Any suitable source of light may be used to introduce light into the receiving ends of fiber bundles 50 in handle 52 or beyond. Typical light sources include incandescent bulbs, light emitting diodes, light reflected from the normal microscope illumination system, laser, electro luminescent panels, etc.

A further embodiment of a speculum-mounted generally lamellar light source is shown in FIGS. 7 and 8. Here, speculum 58 includes arms 60, handle 62 and hook members 64 for restraining the eyelids. A light pipe 65, formed from conventional light pipe materials includes rods 66 extending from handle portion 68 and generally trapezoidal light emitting ends 70. As is usual, the light pipe 65 is internally reflecting except for a line 74 along the surface facing cornea 72.

The partial ring of light produced by light pipe can enter the eye at any predetermined angle between about 0° to 90° to the eye plane by selecting the distance between line 74 on opposite sides of the eye and the orientation of the line toward the eye. The facing surface may be planar or curved, generally conforming to the cornea edge, and may include focussing optics to accomplish a desired beam profile, as desired. Any suitable source of light may be used to introduce light into the light receiving end (not shown) of light pipe 65 in handle 68 or beyond. In an additional alternative, the entire speculum could be fabricated from light pipe material having sufficient flexibility so that the arms can be compressed together and released to retract the eyelids.

In an additional alternative, using the general structure of FIGS. 7 and 8, a line of electro luminescent material could be employed along line 74, with ends 70 being simple supports and power wires running along rods 66 in place of the light pipe materials. While in many cases the light pipes are preferred for higher possible illumination levels, the electro luminescent panels may provide sufficient light for certain forms of eye surgery.

Figure 7A:
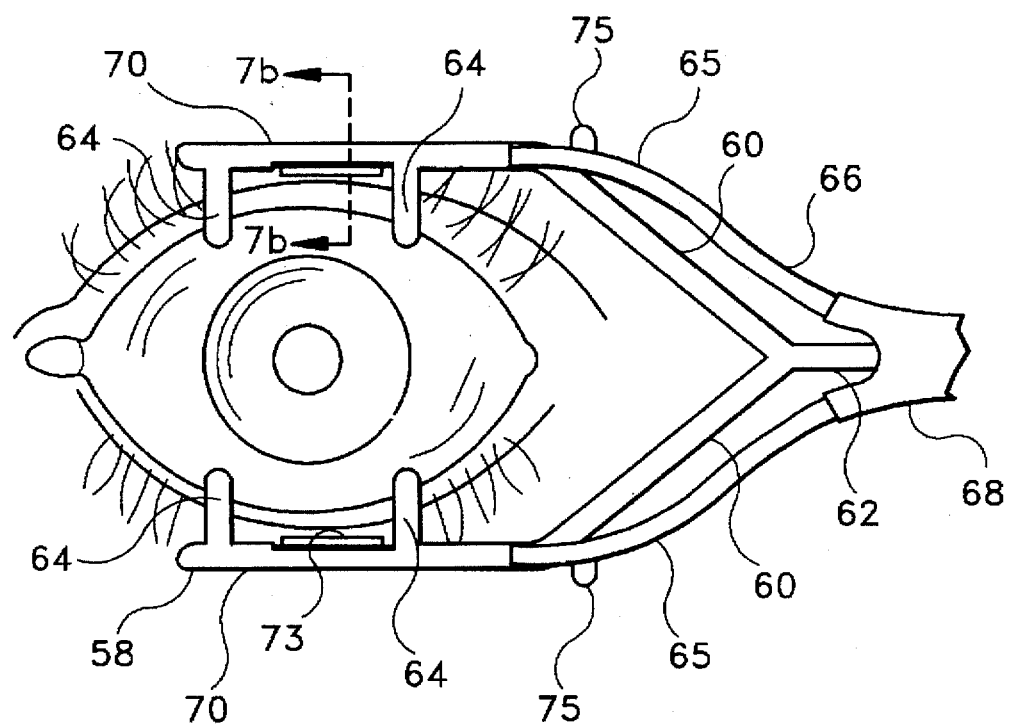
FIG. 7a is a plan view of a variation of the embodiment shown in FIG. 7.
Figure 7B:
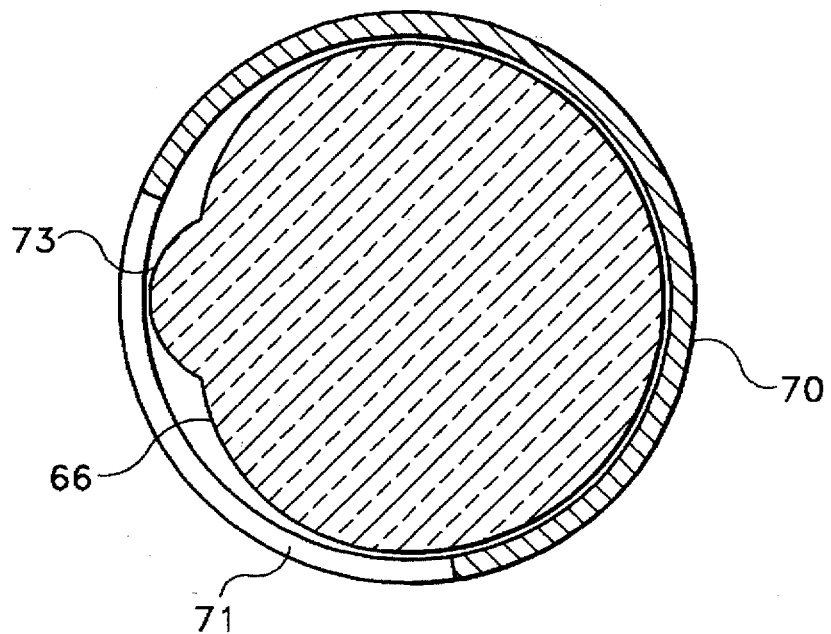

A further variation of the embodiment of FIGS. 7–8 is shown in FIGS. 7a and 7b. Here, the speculum is mounted on arms 60 extending from handle portion 68, with ends 70 being hollow tubes on which hook members 64 are mounted. Ends 70 house and frictionally engage ends of a light pipe 65. An elongated slot 71 is formed along a portion of each end 70, extending radially around a portion of the end 70.

A focussing lens 73 may be an integral part of the light pipe or may be secured to the light pipe end within slot 71 by adhesive bonding or the like. Typically, lens 73 will condense light emitted by light pipe 65 on the surface of the eye or at some other desired distance from the light pipe. By moving tab 75, the focussed beam's angle of incidence could be changed to any desired angle between 0° and 90°.

If desired, lens 75 may be omitted and the surface of light pipe 65 could be coated with an opaque material, leaving an uncoated, light transmitting line corresponding to the base of lens 75. That light emitting line could be moved transverse to the length of slot 71 by manually moving tab 75. With this version, slot 71 could be replaced with a plurality of spaced, parallel slots, so that the light pipe could be rotated to align the light emitting line with any individual slot, so that light would be emitted at a precise selected angle.

A tab 75 is fastened to light pipe 65 adjacent to end 70 so that the light pipe can be rotated to move focussing lens 75 along slot 71 so that the light can be concentrated at an angle to the iris plane of from about 0° to 90°. Of course, any of the other illumination means described herein, such as LED's and the like could be used in this embodiment in a manner similar to the other speculum embodiments.

An embodiment of the apparatus for illuminating the eye by generally lamellar lighting which uses a fixation ring is shown in FIGS. 9 and 10. A ring 76, sized to fit around and near a cornea, is mounted on a handle 78. Fiber optic bundles (or single thicker optical fibers) 80 extend along handle 78 and terminate in light emitting ends 82 positioned to introduce generally lamellar light into the eye, at the angles described above. The fiber optics may be supported either along the exterior of handle 78 or in a longitudinal opening in handle 78, as desired. While any suitable number of fiber optic bundles 80 may be used, two as shown are effective. If desired, the fiber optic bundles 80 may run alongside handle 78 as shown or may extend up through a hollow handle to a light source. Alternatively, a light source within the handle could be optically reflected down a hollow channel within the handle and reflected to exit at the desired angle of illumination. Further, a fixation ring may be hingedly fixed to the handle or other support means to provide an adjustable angle of light emanating from the support means toward the cornea. Any of the light sources mentioned above may be used. The ends 82 of the fiber optics may be spaced apart and bent to form a partial ring of light projected toward the eye at any desired angle between 0° and 90°.

FIGS. 11 and 12 show a light pipe version of the fixation ring assembly shown in FIGS. 9 and 10, where handle 84 and ring 86 are formed from conventional light pipe material, such as coated acrylic or other suitable materials. Light from an appropriate source enters the distal end of handle 84 (not shown) as described above, and passes around ring 86. As seen in FIG. 12, a bevel 88 is shaped to emit light at the desired angle, preferably 0° to 90° to the iris plane as described above. Thus, ring 86 acts both as a fixation ring around a cornea during surgery and the light source.

FIGS. 13 and 14 show a particularly preferred version of a fixation ring type instrument. Here a ring 90, preferably a 270° segment of a circle, includes two guides 92 which form a 90° included angle. Two projecting stops 94 are provided at the desired location along guides 92. In radial keratotomy using the so-called "Russian" method, a diamond surgical blade mounted in a holder is moved along guides 94 toward the center of the cornea. After producing two radial incisions the ring 90 may then be rotated and two additional radial incisions made. With ring 90 centered on the eye, the blade holder will be stopped at the precise desired location by stops 94, to prevent cutting into the visual axis of the eye.

Ring 90 is pivotally mounted on two arms 96 which are in turn mounted on handle 98. Two fiber optic bundles 100 extend down through opening in handle 98 (or, if desired along the exterior of the handle) to light emitting ends 104. When ring 90 is in place on an eye handle 104 can be tilted and the ends 104 and angled and spaced to provide any desired angle to the iris plane, within the 0° to 90° range, to produce optimum illumination.

Any suitable light source may be used, as detailed above. If desired, batteries and a light source such as an incandescent bulb, light emitting diode or the like may be enclosed within handle 98. The terminal end 100 may be replaced with an optical means to create a generally linear beam of light directed at the desired angle.

An embodiment of a fixation ring including light emitting and position stabilizing means is shown in FIGS. 15 and 16. Ring 106 is a light pipe ring generally similar to that shown in FIGS. 11 and 12, but with flat, parallel, upper and lower surfaces and a light emitting surface on the inner surface. A light pipe 107 is optically connected to ring 106 and extends to a light source (not shown) of the sort detailed above.

Handle 107 may be formed from a flexible material which can be secured to any nearby support means, so that the ring assembly is pressed against the eye without any requirement that the handle be physically held by a person. Further, handle 107 may be adjustable or flexible so that the end of the handle can be fastened to other structures, such as an eyelid speculum, with a ball and socket or other movable mount.

A coextensive channel ring 108 is secured to ring 106 with the channel open side adapted to be placed on the surface of an eye. Ring 108 is formed from a soft rubbery material, such as a silicone rubber. When pressed against the eye surface around a cornea, ring 108 will deform slightly and provide a "suction cup" effect. Preferably the inner leg of the ring channel is slightly shorter than the outer ring to generally conform to the eye curvature. Ring 106 can be simply rested upon the eye or could be affixed in a hinged manner to another support means, such as an eyelid speculum. The inside surface of ring 106 can be configured to provide any desired impingement angle to the eye plane in the 0° to 90° range.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. Apparatus for illuminating the interior of an eye by lamellar visible light during eye surgery which comprises:
   support means for placing in contact with, or close proximity to, an eye adjacent to a surgical field;
   a visible light emitting means mounted on said support means for directing visible light toward said surgical field and into said eye when said support means is in place on an eye; and
   said visible light emitting means oriented to direct said visible light into said eye at an angle from about 0° to 90° to the iris base plane along a path having a predetermined orientation such that light is not refracted into the eye along the eye axis and does not directly pass to the central back portion of the eye.

2. The apparatus according to claim 1 wherein said support means is an eyelid speculum having two opposed arms for retracting opposite eyelids.

3. The apparatus according to claim 2 further including at least one housing on each arm of said speculum, each housing containing a light emitting means and having an opening toward the eye iris through which said light is emitted.

4. The apparatus according to claim 2 further including a light source remote from said speculum and a light directing means selected from the group consisting of reflective optics and refractive optics for directing light from said light source to said light emitting means.

5. The apparatus according to claim 4 wherein said optics are selected from the group consisting of fiber optics and light pipes.

6. The apparatus according to claim 2 wherein said light source comprises a light emitting diode.

7. The apparatus according to claim 1 wherein said support means is a fixation ring assembly including a ring for engaging a surface of an eye and a handle secured thereto.

8. The apparatus according to claim 7 further including a light source remote from said fixation ring and a light directing means selected from the group consisting of reflective optics and refractive optics for directing light from said light source to said light emitting means.

9. The apparatus according to claim 8 wherein said optics are selected from the group consisting of, fiber optics and light pipes.

10. The apparatus according to claim 7 wherein said light source is selected from the group consisting of incandescent lamps, lasers, electro luminescent means and light emitting diodes.

11. The apparatus according to claim 10 further including a soft plastic ring-like channel means secured to one planar surface of said ring, whereby when said channel is pressed against a surface of an eye said ring will be held thereto.

12. Apparatus for illuminating an eye by generally lamellar lighting during eye surgery which comprises:

an eyelid speculum assembly comprising two spaced arms including means for retracting opposite eyelids away from each other;

at least one of said arms including a light emitting means for directing visible light toward a surgical field between said arms when said retracting means are in engagement with eyelids;

said visible light emitting means variably orientable to direct said light at any angle between about 0° to 90° to the eye iris base plane; and said light emitting means including focussing means oriented offset from the eye pupillary axis sufficiently to direct light into the eye while preventing direct and refracted visible light from entering the pupillary axis.

13. The apparatus according to claim 12 wherein said light emitting means comprises a housing mounted on at least one of said arms, said housing including an opening oriented to direct light at said angle and means for introducing light into said housing.

14. The apparatus according to claim 13 wherein said means for introducing light into said housing is selected from the group consisting of incandescent bulbs, light emitting diodes and light emitting ends of reflective optics and refractive optics and said optics are selected from the group consisting of fiber optics and light pipes.

15. The apparatus according to claim 12 wherein said light emitting means comprises a plurality of fiber optics extending through at least one of said arms from a remote light source and terminating in light emitting ends orientable along said arm to variably direct said light at said directions and angles.

16. The apparatus according to claim 12 wherein said light emitting means comprises at least one light pipe extending along at least one of said arms from a remote light source to an emitting end oriented to variably direct said light at said directions and angles.

17. Apparatus for illuminating the interior of an eye by generally lamellar visible light during eye surgery which comprises:

a fixation ring;

a handle connected to said fixation ring for manipulating said fixation ring;

a visible light emitting means at said fixation ring for directing visible light toward a surgical field within said fixation ring when said fixation ring is in engagement with an eye;

said visible light emitting means oriented to direct said visible light into said eye at an angle of from about 0° to 90° to the eye iris base plane and pass at least a portion of said visible light out of said eye while preventing visible light refraction from the eye surface along the pupillary axis and generally preventing light from directly passing to the central back portion of the eye.

18. The apparatus according to claim 17 wherein said light emitting means comprises at least one optical fiber supported by said handle and oriented to direct said light in said direction at said angle.

19. The apparatus according to claim 17 wherein said fixation ring comprises light pipe material having a surface for emitting light oriented to direct said light in said direction at said angle and having a light pipe optically connected between to said light pipe material and having a distal end for receiving light from a light source.

20. The apparatus according to claim 17 further including a channel ring generally coextensive with said fixation ring and secured therto, said channel ring being formed from a soft, rubbery material and having inner and outer channel legs extending away from fixation ring.

21. The apparatus according to claim 17 wherein said handle is flexible and adjustable and optics are selected from the group consisting of fiber optics and light pipes.

22. The method of illuminating the interior of an eye by generally lamellar visible light which comprises the steps of:

providing a visible light emitting means mounted on a support means;

positioning said support means on or near the surface of said eye adjacent to a surgical field;

orienting said visible light emitting means to direct light into said eye at an angle of from about 0° to 90° to the plane of the eye iris and reflect at least a portion of said visible light out of said eye while avoiding light reflection from the eye surface back along the pupillary axis.

23. Apparatus for illuminating the interior of an eye by lamellar visible light during eye surgery which comprises:

an eyelid speculum including two spaced elongated tubular support means each having a longitudinal axis and each carrying means for retracting eyelids, for placement across an eye;

each support means including at least one longitudinal slot oriented toward an eye when in place on said eye;

visible light emitting means within each said support means for directing visible light through said at least one slot toward said surgical field and into said eye when said speculum means is in place on an eye; and means for rotating each light emitting means about said longitudinal axis to direct light though a selected one of said at least one slot.

24. The apparatus according to claim 23 wherein said slots are orientable at angles to an iris plane in the range of 0° to 90°.

25. The apparatus according to claim 23 further including optical means on said light emitting means for focusing emitted light at a predetermined distance from said light emitting means.

* * * * *